United States Patent [19]

Fozzard

[11] 4,117,242
[45] Sep. 26, 1978

[54] SUPPRESSION OF SIDE REACTIONS IN CATALYTIC HYDROGENATION OF DIESTERS

[75] Inventor: George B. Fozzard, Bartlesville, Okla.

[73] Assignee: Phillips Petroleum Company, Bartlesville, Okla.

[21] Appl. No.: 708,454

[22] Filed: Jul. 26, 1976

[51] Int. Cl.$^2$ ............................................. C07C 67/28
[52] U.S. Cl. .................................... 560/263; 260/409; 260/410; 260/410.6; 560/231
[58] Field of Search .................. 260/491, 410.6, 410, 260/409; 560/263, 231

[56] References Cited

U.S. PATENT DOCUMENTS

| | | | |
|---|---|---|---|
| 2,027,182 | 1/1936 | Lazier | 260/491 |
| 3,849,480 | 11/1974 | Knowles et al. | 260/490 |
| 3,872,163 | 3/1975 | Shimizu et al. | 260/491 |

*Primary Examiner*—Vivian Garner

[57] ABSTRACT

A process is provided for hydrogenation of unsaturated diesters produced by the reaction of conjugated diolefin and monocarboxylic acid in which the diester is contacted with hydrogen in the presence of a noble metal and a monoamine. The presence of the monoamine suppresses hydrogenolysis of the diester to monoester. In a preferred embodiment 1,4-diacetoxy-2-butene is hydrogenated in the presence of a palladium catalyst and a monoamine selected from methylamine, n-butylamine, triethylamine, tripropylamine, quinoline, and toluidine.

6 Claims, No Drawings

SUPPRESSION OF SIDE REACTIONS IN CATALYTIC HYDROGENATION OF DIESTERS

BACKGROUND OF THE INVENTION

This invention relates to hydrogenation processes. In one of its aspects this invention relates to the hydrogenation of unsaturated diesters. In another of its aspects this invention relates to the suppression of side reactions in the hydrogenation of unsaturated diesters. In yet another aspect of the invention it relates to modifying agents for catalytic reactions. In yet another aspect of the invention it relates to the suppression of hydrogenolysis of a diester to the monoester.

The use of polyesters in manufacturing has grown considerably in recent years. With the growth of use of polyesters the means for producing glycols or diols from which polyesters can be formed have also become more important. One method for producing diols is the production of unsaturated diesters, such as those made by the reaction of conjugated diolefins with monocarboxylic acids, with subsequent hydrogenation to produce saturated diesters which upon treatment with an hydroxide yields a diol.

Unfortunately, when this route is taken for producing diols the hydrogenation of the unsaturated diester, although usually proceeding smoothly, is accompanied by a side reaction that is a hydrogenolysis which splits off one of the ester groups to leave a monoester. Since in the production of a diol it is important to produce as high yield of saturated diester as possible, the side reaction should be kept to a minimum. It has now been discovered that the hydrogenolysis can be suppressed by the addition of certain compounds to the reaction mixture in the hydrogenation.

It is therefore an object of this invention to provide a method for hydrogenating unsaturated diesters. It is a more specific object of this invention to provide a method for hydrogenating unsaturated diesters which are made by the reaction of conjugated diolefins with monocarboxylic acids. It is another object of this invention to provide a method for suppressing side reactions, specifically hydrogenolysis, in the hydrogenation of unsaturated diesters.

Other aspects, objects, and the various advantages of this invention will become apparent upon studying the specification and appended claims.

STATEMENT OF THE INVENTION

In accordance with this invention, a method is provided for hydrogenation in which hydrogen is contacted with an unsaturated diester in the presence of a noble metal catalyst and a monoamine.

In another way of stating the invention it can be said that in a process for hydrogenation in which a reaction mixture comprising hydrogen and an unsaturated diester is contacted in the presence of a noble metal catalyst contacting the reaction mixture with the catalyst in the presence of a monoamine provides a method for suppressing hydrogenolysis of the diester to monoester.

Although the process set forth herein is applicable for the hydrogenation of unsaturated diesters, generally it is particularly useful for unsaturated diesters which are made by the reaction of conjugated diolefins and monocarboxylic acids. The conjugated dienes can be straight chain or cyclic dienes and preferably have from 4 to about 8 carbon atoms. Butadiene is a preferred diolefin useful for producing unsaturated diesters by the process of this invention. The monocarboxylic acids preferably can have about 1 to about 10 carbon atoms in addition to the carboxylic acid atom and can be defined by the formula RCOOH where R is an alkyl having about 1 to about 10 carbon atoms. A preferred acid useful in producing diesters in the process of this invention is acetic acid. Using butadiene and acetic acid to exemplify the reaction sequence for producing a diol using the process of this invention the following illustration is offered:

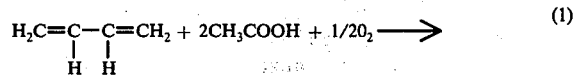

$$CH_3COOCH_2-CH=CH-CH_2OOCCH_3 + H_2O$$

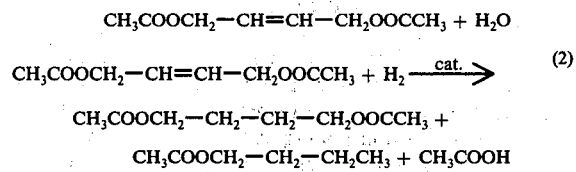

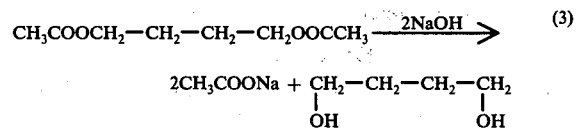

$$2CH_3COONa + CH_2-CH_2-CH_2-CH_2$$
$$\phantom{2CH_3COONa + } | \phantom{CH_2-CH_2-CH_2-} |$$
$$\phantom{2CH_3COONa + } OH \phantom{CH_2-CH_2-CH_2} OH$$

Reactions (1), (2), and (3) shown above are well known in the art. The hydrogenation reaction, reaction (2) is the process of interest in this invention. In this reaction hydrogen is contacted with an unsaturated diester in the presence of a noble metal catalyst. The reaction proceeds at a temperature within the range of about 0° C, preferably about 10° C to about 30° C to about 100° C and at a pressure in the range of about 0.1 atm. (10.1 kPa) to about 100 atm. (10132.5 kPa). In this reaction up to about 75 to 100 weight percent of product can be monoester produced in a side reaction.

In Reaction 2 when carried out in the presence of an amine, especially a tertiary amine, the indicated side reaction to form a monoester will be minimized. General hydrogenation conditions are the same with or without the amine addition. Although the addition of any finite amount of amine will affect the hydrogenation, addition will usually be in the amount of about .05 to about 3.0, preferably in the range of .3 to about 2.0 weight percent of unsaturated diester.

Suitable amines have the formula $RNH_2$, $R_2NH$ or $R_3N$ in which R is straight chain or cyclic having 1–15 carbon atoms. The R's can be the same or different in the secondary and tertiary amines: methylamine, ethylamine, propylamine, n-butylamine, hexylamine, diethylamine, N-ethyl-N-propylamine, dipropylamine, di-tert-butylamine, triethylamine, tripropylamine, tri-hexylamine, N-diethyl-N-propylamine, N-ethyl-N-tert-butyl-N-hexylamine, quinoline, toluidine, decylamine, di-dodecylamine, tri-pentadecylamine, and mixtures of these.

EXAMPLE I

Preparation of 1,4-diacetoxy-2-butene

The hydrogenation experiments were carried out on freshly prepared ester. For test purposes, the diester was made from the diol and acetic acid rather than from butadiene and acetic acid which is the commercial process.

| Materials | |
| --- | --- |
| 2-butene-1,4-diol | 1000 g, 11.36 moles |
| Acetic acid | 1573 g, 26.23 moles |
| Benzene | 700 ml |

The chemicals were introduced into a 5 liter single neck round bottom flask. HCl gas was bubbled into the mixture until it was very acidic; the reaction mixture turned dark. Then the flask was fitted with a magnetic stirrer and a Dean-Stark trap. The mixture was refluxed and water was collected until 510 ml (123% of theory) had been removed. 216 g (2.12 moles) acetic anhydride was then added and the mixture was refluxed for 2 hours to remove the last traces of water and to ensure complete conversion of the diol. The solvent benzene, excess acetic acid and acetic anhydride were removed using a rotary evaporator. The residue was distilled on a 45 theoretical tray laboratory type spinning band column. The fraction boiling at 84° C was collected as product. 1058 g of 99.8 purity material, 1,4-diacetoxy-2-butene was recovered.

EXAMPLE II

A series of batch hydrogenations were run using a 400 ml glass Parr bottle as container. In each run 15 g (0.087 moles) 1,4-diacetoxy-2-butene in 100 ml solvent and 0.3 g catalyst were used. In experimental runs according to the invention 0.1–0.2 g of the amine modifier was added to the mixture. The filled Parr bottle was placed in a shaker, evacuated and flushed 3 times with hydrogen and then pressured with hydrogen to 45 psig. On decrease to about 25 psig the reaction vessel was repressured to about 45 psig. Shaking was started and the pressure drop recorded as a function of time. Reaction started at about 25° C and temperature ranged up to about 35° C. After hydrogen uptake had ceased, the residual hydrogen was removed and the contents filtered to remove the solid catalyst. The product was analyzed by GLC on a tris(2-cyanoethoxy) propane column to determine the amount of 1,4-diacetoxybutane (DABA) and side product butyl acetate produced. Data from the hydrogenation runs are given in Tables I-III.

TABLE I

Hydrogenation of cis 1,4-Diacetoxy-2-butene with Pd/Al$_2$O$_3$*

| | | | | Yield, wt. % | |
| --- | --- | --- | --- | --- | --- |
| Run | Solvent | Modifier | Time[1] Min. | Butyl Acetate | 1,4-DABA |
| 1 | THF (tetrahydrofuran) | None | 10 | 7 | 93 |
| 2 | THF | tripropylamine (~0.1g) | 25 | 1 | 99 |
| 3 | THF | triethylamine (~0.1g) | 7 | 2 | 98 |
| 4 | abs EtOH | None | 10 | 2 | 98 |
| 5 | abs EtOH | triethylamine (~0.1g) | 8 | 2 | 98 |
| 6 | 95% EtOH | triethylamine (~0.1g) | 12 | 3 | 97 |
| 7 | MeOH | None | 3 | 5 | 95 |
| 8 | MeOH | triethylamine (~0.1g) | 4 | 2 | 98 |
| 0 | MeOH | water (10 ml) | 5 | 4 | 96 |

*0.3 to 0.25 g of Englehard 5% Pd/Al$_2$O$_3$
[1]Time required to complete conversion The data in Table I (catalyst Pd on Al$_2$O$_3$) show that the solvent affects the amount of hydrogenolysis which takes place. Tetrahydrofuran (THF) by itself (Run 1) yields 7% by wt. butyl acetate, the hydrogenolysis product. With either triethyl or tripropylamine the butyl acetate yield is reduced to 2 and 3% by wt., respectively, and the yield of the desired product is increased from 93 to 98 and 99 weight percent. Using ethanol, as solvent the initial yield of desired product is 98 weight percent and the addition of the modifier has no effect. With methanol as solvent, the modifier, triethylamine, increases product yield from 95 to 98 weight percent.

TABLE II cis-1,4-Diacetoxy-2-butene Hydrogenation with Pd/C*

| | | | | Yield, wt. % | |
| --- | --- | --- | --- | --- | --- |
| Run | Solvent | Modifier | Time[3] Min. | Butyl Acetate | 1,4-DABA |
| 10 | cyclohexane | None | 5 | 24 | 76 |
| 11 | cyclohexane | 2-NPS[2] 0.1g | 18 | 33 | 67 |
| 12 | cyclohexane | Quinoline 0.2g | 61 | 11 | 89 |
| 13 | CH$_3$OH | None | 4 | 25 | 75 |
| 14 | CH$_3$OH | 2-NPS[2] 0.1g | 8 | 37 | 63 |
| 15 | CH$_3$OH | Quinoline 0.1g | 10 | 22 | 78 |
| 16 | THF | None | 3 | 15 | 85 |
| 17 | THF | 2-NPS[2] 0.1g | 8 | 22 | 78 |
| 18 | THF | Quinoline 0.1g | 111 | 6 | 94 |
| 19 | THF | 5% Water | 5 | 16 | 84 |
| 20 | THF | Tripropylamine ~0.1g | 8 | 5 | 95 |
| 21 | THF | Sodium Acetate 0.1g | 16 | 16 | 84 |
| 22 | THF | 5ml 5% NaOH in H$_2$O | 10 | 18 | 82 |
| 23 | THF | None | 5 | 9 | 91 |
| 24 | THF | n-butylamine 0.2g | 8 | 6.6 | 93.4 |
| 25 | THF | Diethylamine 0.2g | 4 | 6 | 94 |
| 26 | THF | Toluidine 0.2g | 10 | 1.4 | 98.6 |
| 27 | THF | Tetramethylethylenediamine 0.2g | 10 | 27.5 | 72.5 |

*0.5 of Engelhard 5% Pd/C except for run 20 which used 0.3 g
[2]2-NPS = 2-naphthalenesulfonic acid
[3]Time required for complete conversion In Table II, the catalyst is Pd on carbon. In cyclohexane, the modifier quinoline increases product yield from 76 to 89%. 2-naphthalene sulfonic acid, another experimental modifier, not an amine, is detrimental as an additive. This is also true when other solvents such as methanol and THF are used. In all cases, the amine modifiers increase the yield of desired product. The one diamine tested (Run 27) was exceedingly detrimental and no further tests of diamines were run.

TABLE III cis 1,4-Diacetoxy-2-butene Hydrogenation with Pd/CaCO$_3$*

| Run | Solvent | Modifier | Time Min. | Butyl Acetate | 1,4-DABA |
|---|---|---|---|---|---|
| 28 | THF | None | 9 | 1.5 | 98.5 |
| 29 | THF | triethylamine ~0.1g | 9 | 1.6 | 98.4 |
| 30 | abs EtOH | None | 4.5 | 3 | 97 |
| 31 | abs EtOH | triethylamine 0.1g | 6 | 3.6 | 96.4 |

*0.3g of Engelhard 5% Pd/CaCO$_3$. Prereduced for 2 hrs. at 175° C with hydrogen flow.

The data of Table III show that the modifier has no effect when Pd on CaCO$_3$ is used as catalyst.

An improvement in the yield of the desired 1,4-diacetoxybutane is found by the addition of about .1 g - .2 g of a monoamine to a catalytic hydrogenation system having a noble metal catalyst (Pd, Pt) on alumina or carbon support using an inert solvent such as a light hydrocarbon having 4-8 carbon atoms such as butane, hexane, cyclohexane, octane, alcohols having 1-4 C atoms, methyl, ethyl, propyl, isopropyl, butyl alcohols or tetrahydrofuran.

I claim:

1. In a process for hydrogenation in which a reaction mixture comprising hydrogen and an unsaturated diester produced by reaction of hydrocarbon conjugated diolefin chosen from among straight chain and cyclic dienes having 4-8 carbon atoms and monocarboxylic acid chosen from among those defined by the formula RCOOH wherein R is an alkyl group having 1-10 carbon atoms is contacted in the presence of a noble metal catalyst the improvement of contacting said reaction mixture with said catalyst in the presence of a monoamine thereby suppressing hydrogenolysis of said diester to monoester.

2. A process of claim 1 wherein the contacting is in the presence of a solvent inert to said hydrogenation.

3. A process of claim 1 wherein the contacting is carried out under conditions of temperature in the range of about 0° to about 100° C and pressure in the range of about 10.1 kPa to about 10132 kPa.

4. A process of claim 1 wherein said monoamine is a tertiary amine.

5. A process of claim 1 wherein said monoamine is chosen from methylamine, n-butylamine, triethylamine, tripropylamine, quinoline, and toluidine.

6. A process of claim 5 wherein said unsaturated diester is 1,4-diacetoxy-2-butene.

* * * * *

UNITED STATES PATENT AND TRADEMARK OFFICE
CERTIFICATE OF CORRECTION

PATENT NO. : 4,117,242
DATED : September 26, 1978
INVENTOR(S) : George B. Fozzard It is certified that error appears in the above-identified patent and that said Letters Patent are hereby corrected as shown below:

Column 6, line 15, "0°" should be --- 0°C ---.

Signed and Sealed this

Thirteenth Day of March 1979

[SEAL]

Attest:

RUTH C. MASON
Attesting Officer

DONALD W. BANNER
Commissioner of Patents and Trademarks